United States Patent
Swager et al.

(10) Patent No.: US 11,143,613 B2
(45) Date of Patent: Oct. 12, 2021

(54) CHEMIRESISTIVE SENSORS BASED ON CARBON NANOTUBES AND TRANSITION METAL COMPLEXES

(71) Applicant: Massachusetts Institute of Technology, Cambridge, MA (US)

(72) Inventors: Timothy Swager, Newton, MA (US); Sibo Lin, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 251 days.

(21) Appl. No.: 16/275,275

(22) Filed: Feb. 13, 2019

(65) Prior Publication Data

US 2019/0250115 A1    Aug. 15, 2019

Related U.S. Application Data

(60) Provisional application No. 62/630,793, filed on Feb. 14, 2018.

(51) Int. Cl.
*G01N 27/12*    (2006.01)
*G01N 33/00*    (2006.01)
*G01N 33/02*    (2006.01)

(52) U.S. Cl.
CPC ....... *G01N 27/127* (2013.01); *G01N 33/0004* (2013.01); *G01N 33/02* (2013.01)

(58) Field of Classification Search
CPC ... G01N 27/127; G01N 33/0004; G01N 33/02
See application file for complete search history.

(56) References Cited

U.S. PATENT DOCUMENTS 9,995,719 B2    6/2018    Swager et al.
2016/0195504 A1    7/2016    Swager et al.

FOREIGN PATENT DOCUMENTS

WO    2017/209817 A2    12/2017

OTHER PUBLICATIONS

Kaya, Esra Nur, et al. "Effect of pyrene substitution on the formation and sensor properties of phthalocyanine-single walled carbon nanotube hybrids." Sensors and Actuators B: Chemical 199 (2014): 277-283. (Year: 2014).*
Zheng, Li et al. "Electrocatalytic oxidation of methanol and other short chain aliphatic alcohols at Ni (II)-quercetin complex modified multi-wall carbon nanotube paste electrode." Journal of Solid State Electrochemistry 14.1 (2010): 43. (Year: 2010).*
Chaudhuri, Phalguni, et al. "Electronic structure of bis (o-iminobenzosemiquinonato) metal complexes (Cu, Ni, Pd). The art of establishing physical oxidation states in transition-metal complexes containing radical ligands." Journal of the American Chemical Society 123.10 (2001): 2213-2223. (Year: 2001).*

(Continued)

*Primary Examiner* — Robert J Eom
(74) *Attorney, Agent, or Firm* — Honigman LLP

(57) ABSTRACT

A sensor can include a conductive region in electrical communication with at least two electrodes, the conductive region can include a mixture of a square-planar metal complex and a carbon nanotube.

12 Claims, 20 Drawing Sheets

(56) References Cited

OTHER PUBLICATIONS

Gholivand, M.B. et al. "Fabrication of a highly sensitive glucose electrochemical sensor based on immobilization of Ni (II)-pyromellitic acid and bimetallic Au—Pt inorganic-organic hybrid nanocomposite onto carbon nanotube modified glassy carbon electrode." Electrochimica acta 76 (2012): 300-311. (Year: 2012).*
International Search Report and Written Opinion for PCT/US2019/017906 dated Apr. 15, 2019.
(Fratoddi, I et al.) Electrical and morphological characterization of poly(monosubstituted) acetylene based membranes; application as humidity and organic vapors sensors. Thin Solid Films, vol. 458, No. 1-2, pp. 292-298. Jun. 30, 2004.
(Ciccione, J et al.) Geometric and Electronic Structures of Nickel(II) Complexes of Redox Noninnocent Tetradentate Phenylenediamine Ligands. Inorganic Chemistry, vol. 55, No. 2 Dec. 21, 2015.
(Zhang, et al.) Electrocatalytic oxidation of formaldehyde and formic acid at Pd nanoparticles modified glassy carbon electrode. Micro and Nano Letters, vol. 8, No. 10.01 Oct. 2013.
(Swager, TM) Carbon nanotube based chemical sensor, MIT ILP conference, Tokyo, Japan. Jan. 26, 2018. [Retrieved from the internet on Mar. 28, 2019]. <URL: http://ilp.mit.edu/images/conferencesl2018/japan/presentations/Swager.2018.Japan.pdf>.
(Chen, Z-K et al.) The fabrication and evaluation of a vapour sensor based on quartz crystal microbalance coated with poly(o-anisidine) Langmuir-Blodgett layers. Synthetic Metals, vol. 87, No. 3, pp. 201-204. Apr. 15, 1997.

* cited by examiner a b

CNT + *x* applications of selector 1
*x* = 0, 1, 2, 3, 4, 5, 6

CHEMIRESISTIVE SENSORS BASED ON CARBON NANOTUBES AND TRANSITION METAL COMPLEXES

PRIORITY CLAIM

The application claims priority from U.S. Provisional Patent Application No. 62/630,793, filed Feb. 14, 2018, which is incorporated by reference in its entirety.

FEDERALLY SPONSORED RESEARCH OR DEVELOPMENT

This invention was made with Government support under Grant No. DMR1410718 awarded by the National Science Foundation. The Government has certain rights in the invention.

TECHNICAL FIELD

The invention features a chemiresistive sensor.

BACKGROUND

Methods for monitoring for an analyte, such as chromatography, spectrometry, electrophoresis, colorimetry, mass balance, chemiluminescence, and electrochemistry, suffer from one or more drawbacks.

SUMMARY

In one aspect, a sensor can include a conductive region in electrical communication with at least two electrodes, the conductive region including a mixture of a square-planar metal complex and a carbon nanotube.

In certain circumstances, the square-planar metal complex can include a nickel complex or a palladium complex.

In certain circumstances, the square-planar metal complex can include phenylenediamine.

The complex can be a diiminosemiquinonate or derivative thereof.

In certain circumstances, the carbon nanotube can be non-covalently functionalized by the square-planar metal complex.

In certain circumstances, the carbon nanotube can be a single-walled carbon nanotube.

In another aspect, a method of sensing an analyte can include exposing a sensor to a sample, the sensor including a conductive region in electrical communication with at least two electrodes, the conductive region including a mixture of a square-planar metal complex and a carbon nanotube, and measuring an electrical property at the electrodes.

In certain circumstances, the method can include detecting formic acid.

In certain circumstances, the method can include selectively detecting formic acid. For example, formic acid can be distinguished from acetic acid.

In certain circumstances, the detection can be semi-reversible.

In certain circumstances, the method can include detecting the analyte below 5 ppm.

In another aspect, a method of preparing a sensor can include forming a complex including a conductive region in electrical communication with at least two electrodes, the conductive region including a mixture of a square-planar metal complex and a carbon nanotube; and placing the conductive material in electrical communication with at least two electrodes.

In another aspect, a food packaging can include a sensor, wherein the sensor includes a conductive region in electrical communication with at least two electrodes, the conductive region including a mixture of a square-planar metal complex and a carbon nanotube.

In certain aspects, the square-planar metal complex can include two or more selectors.

In other aspects, the two or more selectors leverage their chelating N—H moieties to facilitate protonation or p-doping of a CNT chemiresistor network by formic acid vapors.

In other aspects, a low-power carbon nanotube sensor is capable of detecting formic acid at concentrations relevant to industrial settings within 1 minute exposure times based on chemiresistive discrimination between formic and acetic acid vapors.

Other aspects, embodiments, and features will be apparent from the following description, the drawings, and the claims.

BRIEF DESCRIPTION OF THE DRAWINGS

In FIG. 2B, each trace (vertically offset for clarity) is the average of four sensors with the standard deviation illustrated in a lighter shade; five cycles of one-minute exposure and nine-minute purge. The carrier gas is $N_2$ unless otherwise noted. In FIG. 2C, average conductivity change for each selector is shown. Error bars represent one standard deviation across 20 data points (five measurements each across four devices).

DETAILED DESCRIPTION

Figure 1A:
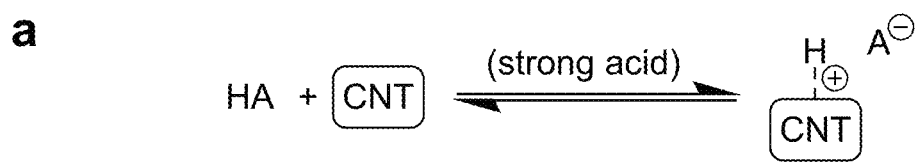
FIGS. 1A-1B show carbon nanotube protonation and p-doping by (FIG. 1A) strong acid or (FIG. 1B) carboxylic acid assisted by anion receptor.

In one aspect, square planar transition metal complexes can be brought in contact with carbon nanotubes to create chemical sensors with high sensitivity and selectivity. The direct contact of the metal complexes with the carbon nanotubes and the comingling of their electronic states is a key feature. The compounds reported are sterically unencumbered to maximize this interaction. For comparison, porphyrins contain substituents that sterically buttress the metal centers from making similar levels of contact. As shown herein, the binding of an analyte to the ligand can affect the conductance. In certain embodiments, there can be cases wherein direct analyte interaction with the metal center may also be used to create selective sensor responses. The invention is demonstrated by using the selective hydrogen bonding to formic acid, however similar interaction mechanisms could be developed for a variety of analytes.

A sensor can include a conductive region in electrical communication with at least two electrodes. The electrodes can be a metal, for example, an inert metal, conductive oxide, doped semiconductor or conductive polymer. The conductive region can include a mixture of a square-planar metal complex and a carbon nanotube. The carbon nanotube can be a multi-walled carbon nanotube or a single-walled carbon nanotube. The square-planar complex can include a transition metal with a ligand, for example, a bidentate or tridentate ligand. For example, the square-planar metal complex can include a nickel complex or a palladium complex.

The ligand can be a polyamino ligand, such as, for example, phenylenediamine or diiminosemiquinonate, or derivative thereof. In certain aspects, the square-planar metal complex can include two or more selectors. In other aspects, the two or more selectors leverage their chelating N—H moieties to facilitate protonation or p-doping of a CNT chemiresistor network by formic acid vapors. For example, the selector can include a diaminoaromatic.

The carbon nanotube can interact with the square-planar complex. For example, the carbon nanotube can be non-covalently functionalized by the square-planar metal complex.

A method of sensing an analyte can include exposing a sensor to a sample, the sensor including a conductive region in electrical communication with at least two electrodes, the conductive region including a mixture of a square-planar metal complex and a carbon nanotube, and measuring an electrical property at the electrodes.

The method can include detecting an organic acid, for example, acetic acid or formic acid. In certain circumstances, the method can include selectively detecting formic acid. For example, formic acid can be distinguished from acetic acid.

In certain circumstances, the detection can be semi-reversible.

In certain circumstances, the method can include detecting the analyte below 5 ppm.

The sensor can be prepared by forming a complex including a conductive region in electrical communication with at least two electrodes, the conductive region including a mixture of a square-planar metal complex and a carbon nanotube; and placing the conductive material in electrical communication with at least two electrodes.

The sensor described herein can be used in food packaging.

In other aspects, a low-power carbon nanotube sensor is capable of detecting formic acid at concentrations relevant to industrial settings within 1 minute exposure times based on chemiresistive discrimination between formic and acetic acid vapors.

Formic acid, the simplest organic acid, is highly pungent and corrosive with a Permissible Exposure Limit (U.S. OSHA PEL) of 5 ppm. An inexpensive, real-time, electronic sensor for formic acid vapors can protect worker health and limit formicary corrosion of metal components. See, e.g., Mikhailov, A. A. Effect of Low-Molecular Carbon Acids on Atmospheric Corrosion of Metals. Prot. Met. Phys. Chem. Surfaces 2009, 45 (7), 757-765. Formic acid sensors can also be useful in diagnosing health conditions monitoring air quality, tracking the spread of invasive formicine ant species such as *Nylanderia fulva* ("tawny crazy ant"), and enabling automated pest control. See, e.g., Greenwald, R.; Johnson, B. A.; Hoskins, A.; Dworski, R. Exhaled Breath Condensate Formate after Inhaled Allergen Provocation in Atopic Asthmatics In Vivo. J. Asthma 2013, 50 (6), 619-622; Greenwald, R., Fitzpatrick, A. M.; Gaston, B.; Marozkina, N. V.; Erzurum, S.; Teague, W. G. Breath Formate Is a Marker of Airway S-Nitrosothiol Depletion in Severe Asthma. PLoS One 2010, 5 (7), e11919; McMartin, K. E.; Ambre, J. J.; Tephly, T. R. Methanol Poisoning in Human Subjects. Role for Formic Acid Accumulation in the Metabolic Acidosis. Am. J. Med. 1980, 68 (3), 414-418; Yan, Y.; Lu, D.; Zhou, H.; Hou, H.; Zhang, T.; Wu, L.; Cai, L. Polyaniline-Modified Quartz Crystal Microbalance Sensor for Detection of Formic Acid Gas. Water, Air, Soil Pollut. 2012, 223 (3), 1275-1280; Nielsen, G. D.; Hansen, L. F.; Andersen, B.; Poulsen, N. and O. M. Indoor Air Guideline Levels for Formic, Acetic, Propionic and Butyric Acid. Indoor Air 1998, 8 (S5), 8-24; Stavrakou, T.; Müller, J.-F.; Peeters, J.; Razavi, A.; Clarisse, L.; Clerbaux, C.; Coheur, P.-F.; Hurtmans, D.; De Mazière, M.; Vigouroux, C.; et al. Satellite Evidence for a Large Source of Formic Acid from Boreal and Tropical Forests. Nat. Geosci. 2011, 5 (1), 26-30; Wang, Z.; Moshman, L.; Kraus, E.; Wilson, B.; Acharya, N.; Diaz, R. A Review of the Tawny Crazy Ant, *Nylanderia Fulva*, an Emergent Ant Invader in the Southern United States: Is Biological Control a Feasible Management Option? Insects 2016, 7 (4), 77. Sensors would facilitate the adoption of formic acid as a hydrogen carrier for energy storage. Sordakis, K.; Tang, C.; Vogt, L. K.; Junge, H.; Dyson, P. J.; Beller, M.; Laurenczy, G. Homogeneous Catalysis for Sustainable Hydrogen Storage in Formic Acid and Alcohols. Chem. Rev. 2017, acs.chemrev.7b00182. While much work has been done on low-power aqueous-phase pH sensors, volatile acidity detectors have been less explored. Besteman, K.; Lee, J. O.; Wiertz, F. G. M.; Heering, H. A.; Dekker, C. Enzyme-Coated Carbon Nanotubes as Single-Molecule Biosensors. Nano Lett. 2003, 3 (6), 727-730; Fu, Q.; Liu, J. Integrated Single-Walled Carbon Nanotube/microfluidic Devices for the Study of the Sensing Mechanism of Nanotube Sensors. J. Phys. Chem. B 2005, 109 (28), 13406-13408; Li, C. A.; Han, K. N.; Pham, X.-H.; Seong, G. H. A Single-Walled Carbon Nanotube Thin Film-Based pH-Sensing Microfluidic Chip. Analyst 2014, 139 (8), 2011; Gou, P.; Kraut, N. D.; Feigel, I. M.; Bai, H.; Morgan, G. J.; Chen, Y.; Tang, Y.; Bocan, K.; Stachel, J.; Berger, L.; et al. Carbon Nanotube Chemiresistor for Wireless pH Sensing. Sci. Rep. 2015, 4 (1), 4468A selective formic acid detector should be able to discriminate it from other polar compounds. For example, formic and acetic acid are present in similar quantities in environmental and human breath samples and their discrimination has utility.[4] See, e.g., Khare, P.; Kumar, N.; Kumari, K. M.; Srivastava, S. S. Atmospheric Formic and Acetic Acids: An Overview. Rev. Geophys. 1999, 37 (2), 227-248.

Carbon nanotube (CNT)-based chemiresistors are an attractive platform for developing gas sensors. Although colormetric (see, e.g., Sensidyne Industrial Health & Safety Information. Formic Acid 1-50 ppm Gas Detector Tube, at www.sensidyne.com/colorimetric-gas-detector-tubes/detector-tubes/216s-formic-acid.php (last accessed Feb. 12, 2019; Grant, W. M. Colorimetric Microdetermination of Formic Acid Based on Reduction to Formaldehyde. Anal. Chem. 1948, 20 (3), 267-269; Genovese, M. E.; Colusso, E.; Colombo, M.; Martucci, A.; Athanassiou, A.; Fragouli, D. Acidochromic Fibrous Polymer Composites for Rapid Gas Detection. J. Mater. Chem. A 2017, 5 (1), 339-348) and metal-oxide and -nitride chemiresistors (e.g., Eckshtain-Levi, M.; Capua, E.; Paltiel, Y.; Naaman, R. Hybrid Sensor Based on AlGaN/GaN Molecular Controlled Device. ACS Sensors 2016, 1 (2), 185-189) for formic acid detection exist, CNT chemiresistors are cost-effective, low-power, and operational at room temperature. See, e.g., Schnorr, J. M.; Swager, T. M. Emerging Applications of Carbon Nanotubes. Chemistry of Materials. American Chemical Society Feb. 8, 2011, pp 646-657; Snow, E. S.; Perkins, F. K.; Robinson, J. A. Chemical Vapor Detection Using Single-Walled Carbon Nanotubes. Chem. Soc. Rev. 2006, 35 (9), 790; Kauffman, D. R.; Star, A. Carbon Nanotube Gas and Vapor Sensors. Angew. Chem. Int. Ed. 2008, 47 (35), 6550-6570. CNT chemiresistors can be straightforwardly integrated with electronic devices, making them ideal candidates for distributed sensor networks. See, e.g., Ishihara, S.; Labuta, J.; Nakanishi, T.; Tanaka, T.; Kataura, H. Amperometric Detection of Sub-Ppm Formaldehyde Using Single-Walled Carbon Nanotubes and Hydroxylamines: A Referenced Chemiresistive System. ACS Sensors 2017, 2 (10), 1405-1409; Zhu, R.; Azzarelli, J. M.; Swager, T. M. Wireless Hazard Badges to Detect Nerve-Agent Simulants. Angew. Chem. Int. Ed. 2016, 55 (33), 9662-9666.

Figure 1B:
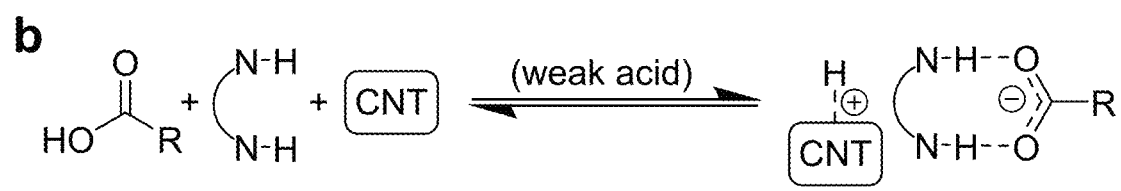

Referring to FIGS. 1A-1B, carbon nanotube protonation and p-doping by (FIG. 1A) strong acid or (FIG. 1B) a weak acid, such as carboxylic acid assisted by anion receptor is depicted.

While strong acids have been shown to protonate and p-dope CNTs (FIG. 1A) (e.g., Parra-Vasquez, A. N. G.; Behabtu, N.; Green, M. J.; Pint, C. L.; Young, C. C.; Schmidt, J.; Kesselman, E.; Goyal, A.; Ajayan, P. M.; Cohen, Y.; et al. Spontaneous Dissolution of Ultralong Single- and Multiwalled Carbon Nanotubes. ACS Nano 2010, 4 (7), 3969-3978; Davis, V. A.; Parra-Vasquez, A. N. G.; Green, M. J.; Rai, P. K.; Behabtu, N.; Prieto, V.; Booker, R. D.; Schmidt, J.; Kesselman, E.; Zhou, W.; et al. True Solutions of Single-Walled Carbon Nanotubes for Assembly into Macroscopic Materials. Nat. Nanotechnol. 2009, 4 (12), 830-834; Strano, M. S.; Huffman, C. B.; Moore, V. C.; O'Connell, M. J.; Haroz, E. H.; Hubbard, J.; Miller, M.; Rialon, K.; Kittrell, C.; Ramesh, S.; et al. Reversible, Band-Gap-Selective Protonation of Single-Walled Carbon Nanotubes in Solution. J. Phys. Chem. B 2003, 107 (29), 6979-6985; Puech, P.; Hu, T.; Sapelkin, A.; Gerber, I.; Tishkova, V.; Pavlenko, E.; Levine, B.; Flahaut, E.; Bacsa, W. Charge Transfer between Carbon Nanotubes and Sulfuric Acid as Determined by Raman Spectroscopy. Phys. Rev. B 2012, 85 (20), 205412) there have been few reports of the chemiresistive response of CNTs to carboxylic acids. Specifically, vertically aligned CNT arrays have a chemicapacitive response to formic acid. See, e.g., Chen, Y.; Meng, F.; Li, M.; Liu, J. Novel Capacitive Sensor. Fabrication from Carbon Nanotube Arrays and Sensing Property Characterization. Sensors Actuators B Chem. 2009, 140 (2), 396-401. Chemical-vapor-deposition-grown graphene becomes more conductive upon exposure to acetic acid vapor. See, e.g., Nallon, E. C.; Schnee, V. P.; Bright, C.; Polcha, M. P.; Li, Q. Chemical Discrimination with an Unmodified Graphene Chemical Sensor. ACS Sensors 2016, 1 (1), 26-31. A single-CNT field effect transistor (FET) responds to propanoic acid vapors upon functionalization with guanine-rich single-stranded DNA. See, e.g., Staii, C.; Johnson, Alan T., J.; Chen, M.; Gelperin, A. DNA-Decorated Carbon Nanotubes for Chemical Sensing. Nano Lett. 2005, 5 (9), 1774-1778. However, these device architectures require greater manufacturing and operating complexity than chemiresistors based on solution-processed networks of CNTs. Networks of covalently-modified CNTs have been reported to increase in resistance, non-selectively, on exposure to acetic acid or other volatile organics via a swelling mechanism. See, e.g., Niu, L.; Luo, Y.; Li, Z. A Highly Selective Chemical Gas Sensor Based on Functionalization of Multi-Walled Carbon Nanotubes with Poly(ethylene Glycol). Sensors Actuators B Chem. 2007, 126 (2), 361-367; Hines, D.; Rümmeli, M. H.; Adebimpe, D.; Akins, D. L. High-Yield Photolytic Generation of Brominated Single-Walled Carbon Nanotubes and Their Application for Gas Sensing. Chem. Commun. 2014, 50 (78), 11568-11571. Studies on CNT-based vapor sensors discriminating between formic and other carboxylic acids are lacking.

Planar ditopic complexes have been investigated as selectors to improve the sensitivity and selectivity of CNT-based sensors toward formic acid. Selectors bearing ditopic hydrogen-bond donors could promote protonation of CNTs by carboxylic acids by stabilizing the carboxylate anion (FIG. 1B). Looking to Nature's formate dehydrogenase for selector inspiration, the highly conserved Arg587 residue is known to be crucial in formate binding as a ditopic hydrogen bond donor. See, e.g., Hartmann, T.; Schrapers, P.; Utesch, T.; Nimtz, M.; Rippers, Y.; Dau, H.; Mroginski, M. A.; Haumann, M.; Leimkühler, S. The Molybdenum Active Site of Formate Dehydrogenase Is Capable of Catalyzing C—H Bond Cleavage and Oxygen Atom Transfer Reactions. Biochemistry 2016, 55 (16), 2381-2389. Structurally related ureas/thioureas are receptors for carboxylates. See, e.g., Kelly, T. R.; Kim, M. H. Relative Binding Affinity of Carboxylate and Its Isosteres: Nitro, Phosphate, Phosphonate, Sulfonate, and δ-Lactone. J. Am. Chem. Soc. 1994, 116 (16), 7072-7080; Hughes, M. P.; Shang, M.; Smith, B. D. High Affinity Carboxylate Binding Using Neutral Urea-Based Receptors with Internal Lewis Acid Coordination. J. Org. Chem. 1996, 61 (14), 4510-4511; Fan, E.; Van Arman, S. A.; Kincaid, S.; Hamilton, A. D. Molecular Recognition: Hydrogen-Bonding Receptors That Function in Highly Competitive Solvents. J. Am. Chem. Soc. 1993, 115 (1), 369-370. For CNT-based chemiresistors, previous work has shown that thioureas can act as effective selectors for cyclohexanone, and the N-aryl substituents are key to transducing a chemiresistive response to CNTs through non-covalent π-π interactions. See, e.g., Schnorr, J. M.; van der Zwaag, D.; Walish, J. J.; Weizmann, Y.; Swager, T. M. Sensory Arrays of Covalently Functionalized Single-Walled Carbon Nanotubes for Explosive Detection. Adv. Funct. Mater. 2013, 23 (42), 5285-5291; Frazier, K. M.; Swager, T.

M. Robust Cyclohexanone Selective Chemiresistors Based on Single-Walled Carbon Nanotubes. Anal. Chem. 2013, 85 (15), 7154-7158.

Figure 2A:
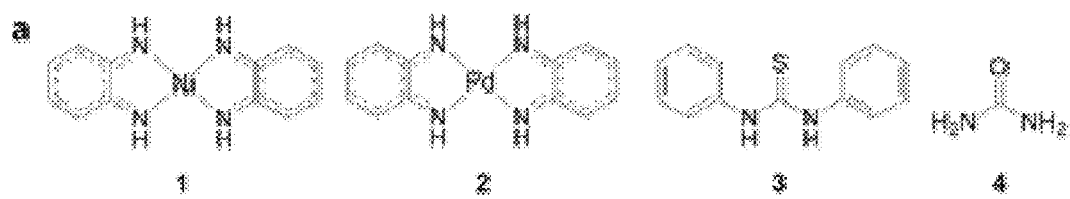
FIGS. 2A-2C show formic acid vapor sensing with CNT chemiresistors and (FIG. 2A) molecular selectors.
Figure 2B:
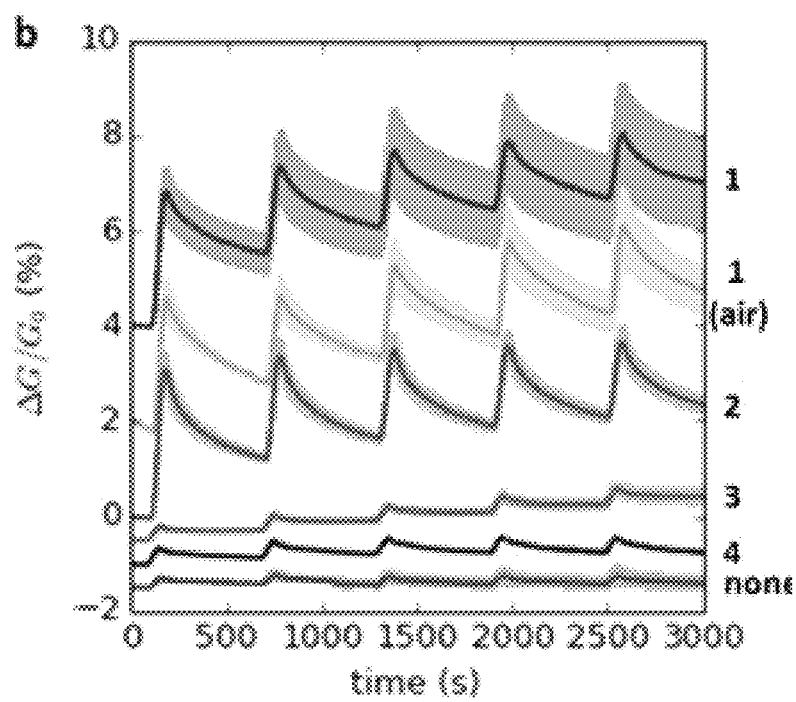
Figure 2C:
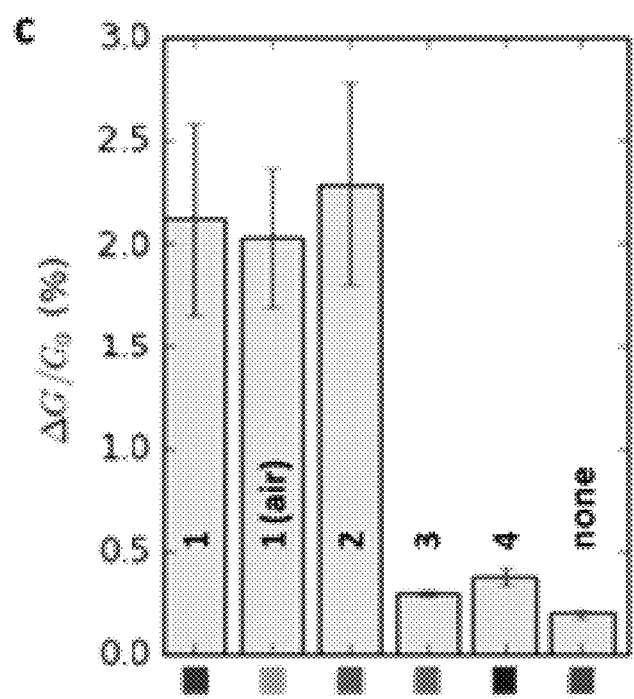

Referring to FIG. 2A-C, formic acid vapor sensing (37 ppm) with CNT chemiresistors is shown. FIG. 2A depicts exemplary molecular selectors. FIG. 2B depicts each trace (vertically offset for clarity) as the average of four sensors with the standard deviation illustrated in a lighter shade, and five cycles of one-minute exposure and nine-minute purge. The carrier gas is $N_2$ unless otherwise noted. FIG. 2C depicts average conductivity change for each selector. Error bars represent one standard deviation across 20 data points (five measurements each across four devices).

Figure 13:
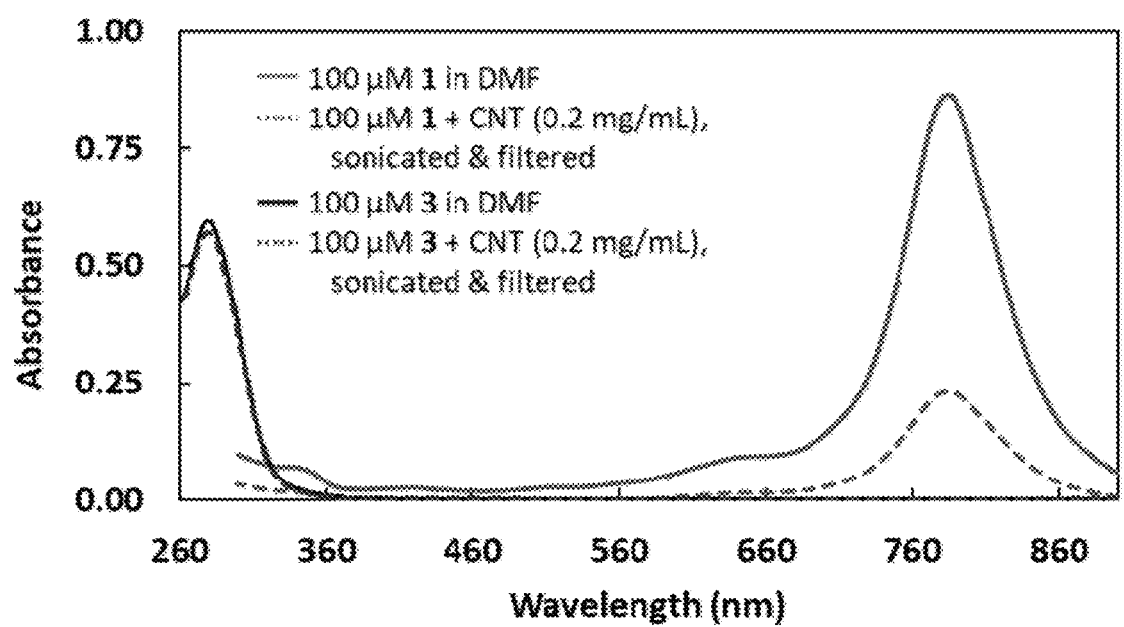
FIG. 13 shows UV-Vis-NIR absorption spectrum of 1 and 3 in DMF before and after sonication with CNT and filtration.

In this study, square planar complexes 1 and 2 (FIG. 2A) were used as selectors. See, e.g., Balch, A. L.; Holm, R. H. Complete Electron-Transfer Series of the [M-N 4] Type. J. Am. Chem. Soc. 1966, 88 (22), 5201-5209. The N—H moieties can participate in ditopic H-bonding with carboxylate, (see, e.g., Bill, E.; Bothe, E.; Chaudhuri, P.; Chlopek, K.; Herebian, D.; Kokatam, S.; Ray, K.; Weyhermülller, T.; Neese, F.; Wieghardt, K. Molecular and Electronic Structure of Four- and Five-Coordinate Cobalt Complexes Containing Two O-Phenylenediamine- or Two O-Aminophenol-Type Ligands at Various Oxidation Levels: An Experimental, Density Functional, and Correlated Ab Initio Study. Chem.-A Eur. J. 2005, 11 (1), 204-224) while the molecular planarity should enhance electronic communication though π-π interactions. See, e.g., Georgakilas, V.; Tiwari, J. N.; Kemp, K. C.; Perman, J. A.; Bourlinos, A. B.; Kim, K. S.; Zboril, R. Noncovalent Functionalization of Graphene and Graphene Oxide for Energy Materials, Biosensing, Catalytic, and Biomedical Applications. Chem. Rev. 2016, 116 (9), 5464-5519; Noro, S. I.; Chang, H. C.; Takenobu, T.; Murayama, Y.; Kanbara, T.; Aoyama, T.; Sassa, T.; Wada, T.; Tanaka, D.; Kitagawa, S.; et al. Metal-Organic Thin-Film Transistor (MOTFT) Based on a Bis(o-Diiminobenzosemiquinonate) nickel(II) Complex. J. Am. Chem. Soc. 2005, 127 (28), 10012-10013. Adding 0-4 equiv. of tetrabutylammonium acetate to 1 in $d^6$-dimethylsulfoxide (DMSO) results in a distinct shift of the N—H protons from 8.8 to 9.2 ppm (see Supporting Information, FIG. 8). This behavior is consistent with competitive H-bonding to acetate and DMSO. UV-Vis-NIR absorption spectra of 1 in N,N-dimethylformamide (DMF) solution show a marked decrease in the LLCT band at 784 nm after exposure to CNTs, indicating strong CNT adsorption of 1 (FIG. 13).

Figure 3A:
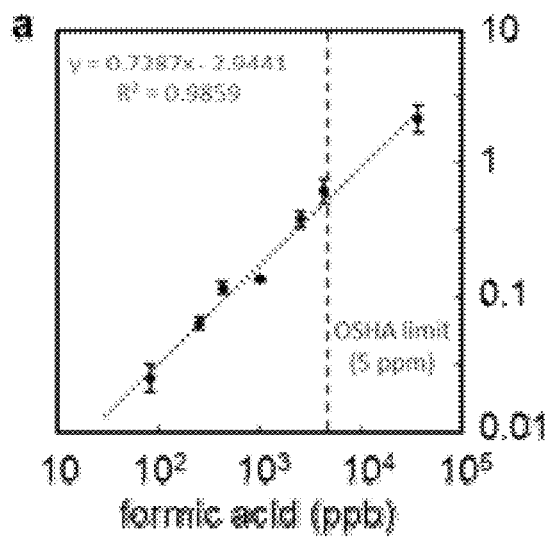
FIGS. 3A-B show average conductivity change (N=20) of CNT/1 upon one-minute exposures to (FIG. 3A) a range of concentrations and (b) various analytes at 2% of their saturated vapor from 40° C. analyte oven.

Chemiresistors made from CNT networks non-covalently functionalized with selector were exposed to formic acid at 37 ppm in $N_2$ at room temperature (2% of its saturated vapor pressure from a calibrated oven held at 40° C.). Analyte exposures were set at 1 minute followed by a 9 minute purge. Devices made with 1 or 2 exhibited semi-reversible 2% increases in conductivity, whereas devices made with N,N'-diphenylthiourea (3), urea (4), or no selector increased conductivity less than 0.4% (FIG. 2B). Because benchtop DMF solutions of 1 remained stable for weeks while those of 2 formed brown particulate, further sensing experiments were conducted with 1 as the selector. An experiment using air (35% relative humidity) as the carrier gas instead of $N_2$ for CNT/1 sensors gave a similar response. We then demonstrated the sensitivity of CNT/1 chemiresistors to formic acid (FIG. 3A). The response is linear for over nearly three orders of magnitude. This dynamic range includes the industrially relevant OSHA PEL of 5 ppm. The experimental limit of detection, 83 ppb, could conceivably be lowered by using longer exposure times.

Figure 3B:
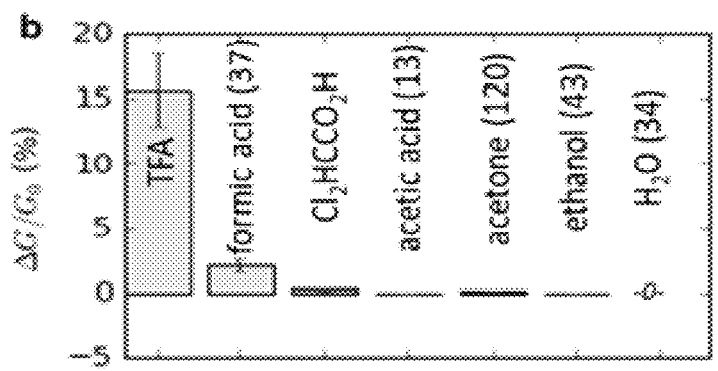

Referring to FIGS. 3A-B, average conductivity change (N=20) of CNT/1 upon one-minute exposures are shown. FIG. 3A shows exposure to a range of concentrations and FIG. 3B shows exposure to various analytes at 2% of their saturated vapor from 40° C. analyte oven. For calibrated analytes, concentrations are listed parenthetically (ppm).

We established the selectivity of CNT/1 chemiresistors by exposure to a variety of other volatile organic compounds at 2% of their saturated vapor pressure from a 40° C. analyte oven (FIG. 3B). Trifluoroacetic acid (TFA), dichloroacetic acid, and acetone induced increases in conductivity per exposure of 16%, 0.23%, and 0.15%. Acetic acid and ethanol resulted in small decreases in conductivity (−0.05% and −0.07%). Water did not cause any change in conductivity. The strong conductivity increase upon TFA exposure correlates with the high acidity of TFA ($pK_a$=0.0). Dichloroacetic acid, while a strong acid ($pK_a$=1.25), has lower volatility and thus a relatively low conductivity increase. Acetic acid is less acidic than formic acid ($pK_a$=4.75 vs 3.75), and the chemiresistive decrease in conductivity is consistent with swelling of inter-CNT gaps, similar to the responses observed for ethanol in this study. Acetic acid vapor also decreased conductivity in previous CNT network chemiresistive sensors.[31,32] As a result, this sensor is selective for formic acid and stronger acids over acetic acid. This selectivity (and reversibility of the response) make CNT/1 chemiresistors unique from sensors based on strong Brønsted bases, which would be irreversible and not distinguish between various carboxylic acids. See, e.g., Yan, Y.; Lu, D.; Zhou, H.; Hou, H.; Zhang, T.; Wu, L.; Cai, L. Polyaniline-Modified Quartz Crystal Microbalance Sensor for Detection of Formic Acid Gas. Water, Air, Soil Pollut. 2012, 223 (3), 1275-1280.

Figure 4A:
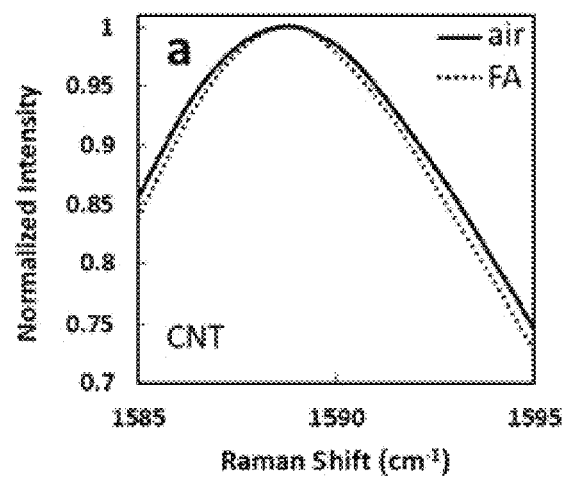
FIGS. 4 A-B shows Raman G-band of (a) CNT and (b) CNT/1 under ambient air or air saturated with formic acid vapor (FA).
Figure 4B:
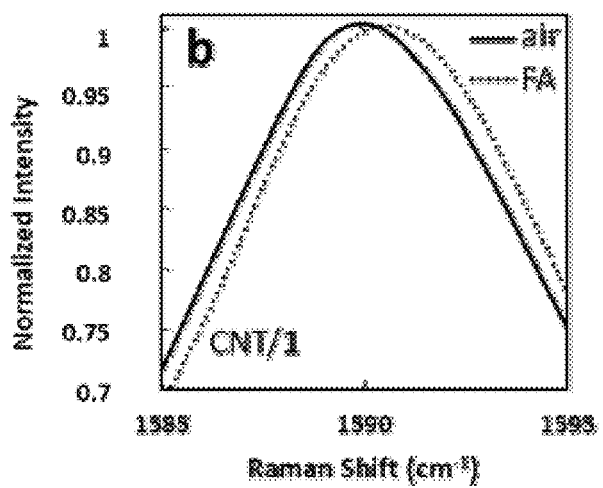

Referring to FIGS. 4A-B, Raman G-band of (a) CNT and (b) CNT/1 under ambient air or air saturated with formic acid vapor (FA) are shown. FIG. 4A is directed to CNT. FIG. 4B is directed to CNT/1.

Figure 14:
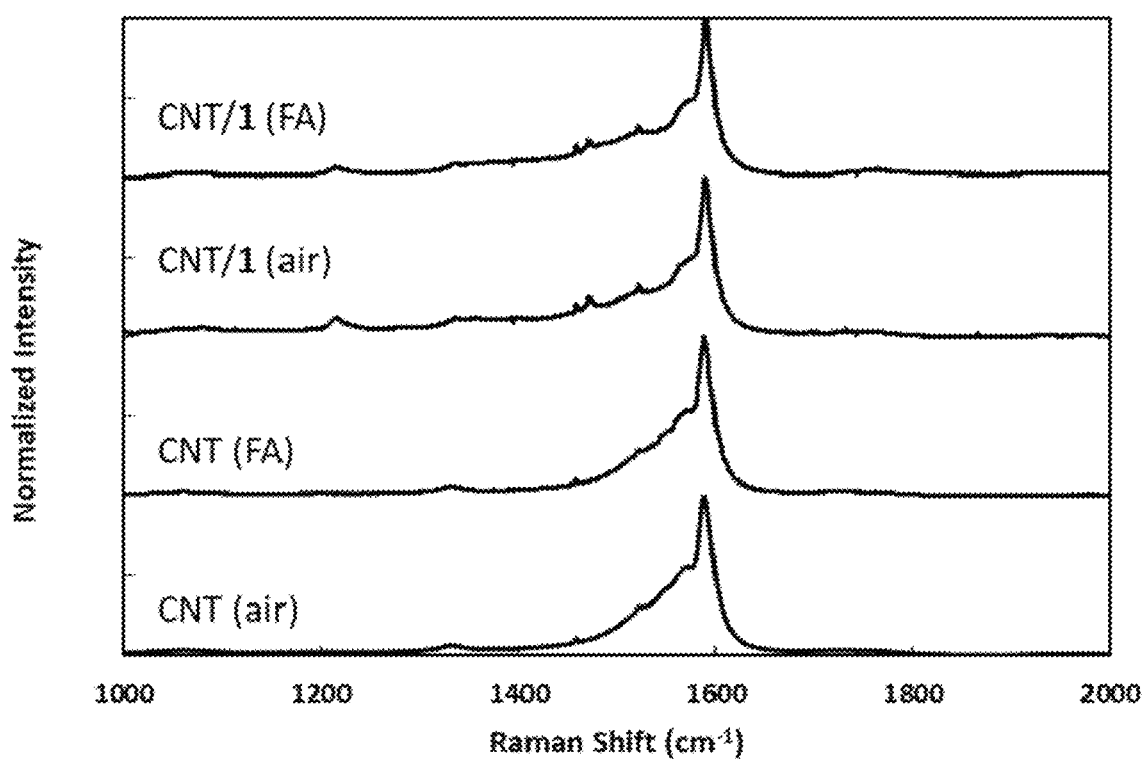
FIG. 14 shows Raman spectra of sensing materials under ambient air or saturated formic acid vapor (FA).
Figure 15:
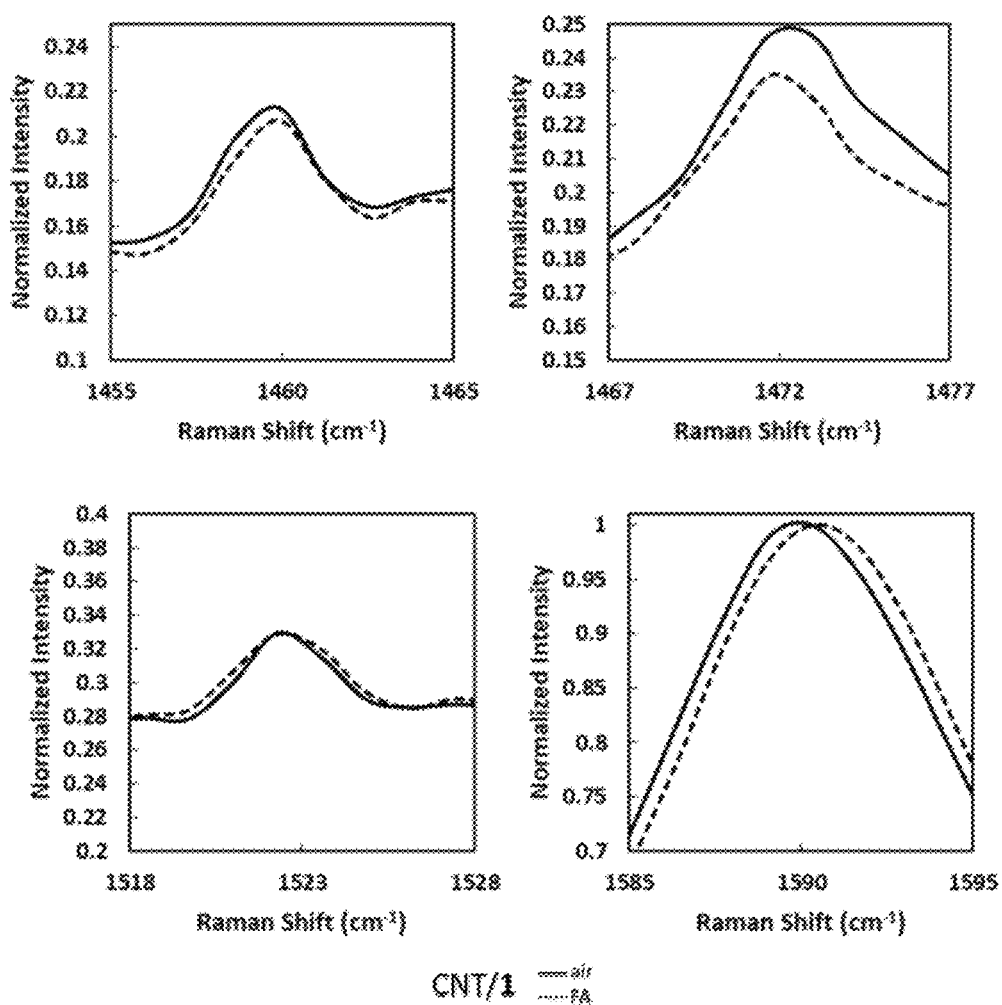
FIG. 15 shows 10 cm-1-wide windows of sharp features of Raman spectra of CNT/1.

To interrogate the mechanism of this chemiresistive response, CNT/1 was examined with Raman spectroscopy (FIG. 14). While the weak CNT D-band (~1340 cm$^{-1}$) is obscured by overlapping signals from 1, the CNT G-band is distinct near 1590 cm$^{-1}$ under ambient air. Under saturated formic acid vapor, however, the G-band shifts to higher energy by 0.5 cm$^{-1}$ (FIG. 4B). Other sharp Raman features of CNT/1 are not similarly shifted (FIG. 15). Based on previous studies of CNTs in acidic solution, (see, e.g., Sumanasekera, G. U.; Allen, J. L.; Fang, S. L.; Loper, A. L.; Rao, A. M.; Eklund, P. C. Electrochemical Oxidation of Single Wall Carbon Nanotube Bundles in Sulfuric Acid. J. Phys. Chem. B 1999, 103 (21), 4292-4297) this shift corresponds to an introduction of approximately one hole per 640 carbon atoms in the CNT sample upon formic acid vapor exposure. Identical measurements of a sample of CNT without 1 showed no shift in the G-band (1589 cm$^{-1}$) under ambient air or formic acid vapor (FIG. 4A). These Raman observations are consistent with 1 facilitating protonation and p-doping of the CNTs.

To investigate the effect of π-stacking between the CNT and 1, we turned to computational models. Although 1 has non-trivial electronic structure as a result of ligand-based radical character, previous studies have shown accurate modeling using density function theory (DFT). See, e.g., Bachler, V.; Olbrich, G.; Neese, F.; Wieghardt, K. Theoretical Evidence for the Singlet Diradical Character of Square Planar Nickel Complexes Containing Two O-Semiquinonato Type Ligands. Inorg. Chem. 2002, 41 (16), 4179-4193; Herebian, D.; Wieghardt, K. E.; Neese, F. Analysis and Interpretation of Metal-Radical Coupling in a Series of Square Planar Nickel Complexes: Correlated Ab Initio and Density Functional Investigation of [Ni(LISQ)2] (LISQ=3, 5-Di-Tert-Butyl-O-Diiminobenzosemiquinonate (1-)). J. Am. Chem. Soc. 2003, 125 (36), 10997-11005. Thus, a segment of (6,6)-CNT and 1 were geometry-optimized using a 2-layer ONIOM scheme in which 1 and the nearest $C_{24}$ fragment (coronene) of the CNT were treated with restricted-spin, dispersion-corrected DFT while the remaining CNT atoms were modelled semiempirically.

Figure 5A:
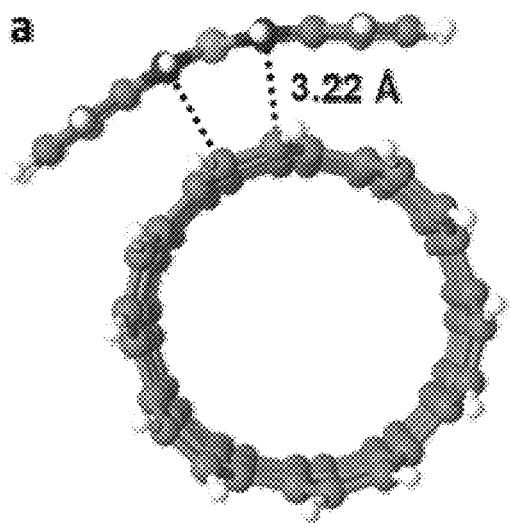
FIGS. 5A-C shows Structural models of (6,6)-CNT/1, (6,6)-CNT/3, and DOS plots of (6,6)-CNT with and without 1 or 3.
Figure 5B:
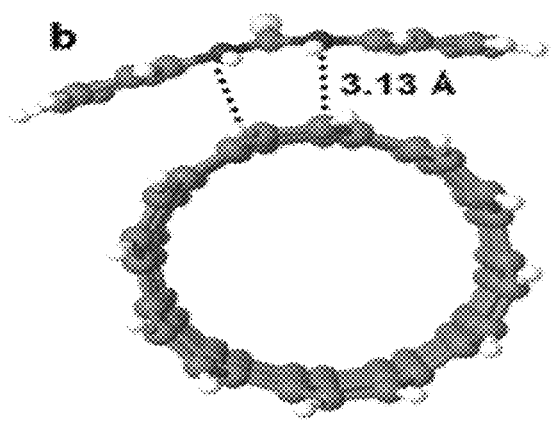
Figure 5C:
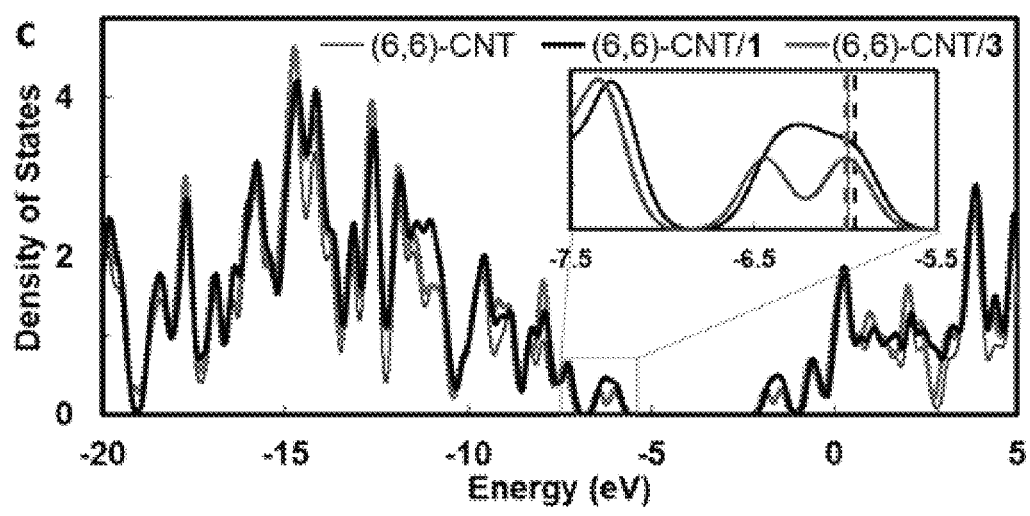

Referring to FIGS. 5A-C, various exemplary structural models are shown. Referring to FIG. 5A, a structural model of (6,6)-CNT/1 is shown Referring to FIG. 5B, a structural model for (6,6)-CNT/3 is shown. Referring to FIG. 5C, DOS plots of (6,6)-CNT with and without 1 or 3 are shown. The graphical inset depicts a magnified view of frontier states with Fermi levels indicated by vertical lines. In the resulting structure, the metal complex adopts the curvature of the underlying CNT (FIG. 5A). Furthermore, the short distance between the N atoms of the metal complex and the nearest CNT atoms (3.22 Å) supports a π-π interaction. The electronic structure was then examined via a single-point calculation, treating the whole model with DFT. The resulting density-of-states (DOS) plot shows a Fermi level of −5.94 eV compared to −5.99 eV for bare (6,6)-CNT (FIG. 5C). Thus, 1 donates partial electron density to the CNT, activating the CNT toward protonation with mild acids. For comparison, an analogous model of (6,6)-CNT/3 also showed short non-bonded N—C contacts (FIG. 5B), but the Fermi level shifts the opposite direction to −6.00 eV, indicating very slight withdrawal of electron density from the CNT. These results corroborate the experimental observation that CNT/1 chemiresistors respond to formic acid more readily than CNT or CNT/3 sensors.

In summary, square-planar metal complex selectors 1 and 2 leverage their chelating N—H moieties to facilitate protonation/p-doping of the CNT chemiresistor network by formic acid vapors. The resulting simple, low-power CNT/1 sensors can detect formic acid at concentrations relevant to industrial settings with short 1 minute exposure times. Although there is cross-reactivity with stronger acids, there is notably a smaller (and inverted) response to acetic acid, establishing the first CNT-based chemiresistive discrimination between formic and acetic acid vapors. Computational models also show that 1 can effectively n-stack and donate partial electron-density into the CNT network. We are interested in extending the use of 1, 2, and related metal complexes as selectors to detect and discriminate isosteres of carboxylate such as bicarbonate, phosphate, and arsenate in aqueous solution.

Figure 6:
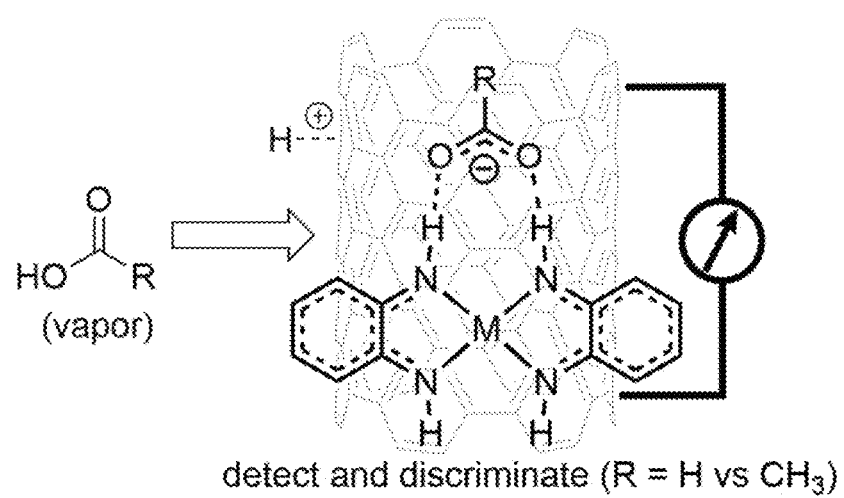
FIG. 6 shows a schematic showing a sensor described herein.

Referring to FIG. 6, a schematic of an exemplary claimed sensor is shown.

Examples

General Considerations

Compounds 1 and 2 were synthesized as reported in the literature. See, e.g., Balch, A. L.; Holm, R. H. Complete Electron-Transfer Series of the [M-$N_4$] Type. *J. Am. Chem. Soc.* 1966, 88 (22), 5201-5209. Single-walled CNTs were purchased from NanoC (UPT-200). All other chemicals, solvents, and analytes (reagent grade) were purchased from commercial suppliers and used without purification. Milligram-scale masses were measured with a Satorius M2P microbalance. See id. H NMR spectra were recorded on 300 MHz and 500 MHz Varian spectrometers and referenced vs. solvent residual signal ($d^6$-DMSO: 2.50 ppm). UV-Vis absorption spectra were recorded with a Cary 4000 UV-Vis-NIR spectrometer. For UV-Vis-NIR samples, after sonication with CNTs, the samples were filtered through a 0.2 Lm PTFE filter to remove insoluble material (i.e. CNTs and any strongly adsorbed species). Raman spectra were recorded with a Horiba HR800 spectrometer on samples enclosed in a quartz cuvette with a small piece of cotton. To generate saturated formic acid vapor conditions (FA), a drop of formic acid was placed on the cotton and the cuvette was carefully capped. Optical microscopy was used to confirm no movement of the Raman sample between ambient air and FA recordings.

Device Preparation

Glass microscope slides were cleaned by immersion in piranha solution for 1 h, followed by sonication in ultrapure water (Milli-Q), sonication in isopropanol, and drying. The slides and a custom stainless steel mask (Stencil.com) were mounted on a substrate holder using screws, and then loaded into an electron-beam physical vapor deposition system (AJA International, ATC-2036). Ti (20 nm) and Au (200 nm) were deposited. Ti was used as the adhesion layer to prevent corrosion that can affect devices made using Cr instead. The resulting microscope slides each contain 14 working electrodes, each separated from a shared counter electrode by a 1 mm gap.

A vial containing 1 mg of CNTs in 4 mL of o-dichlorobenzene was bath-sonicated. Using a micropipette, 1 µL of this solution was placed on each of the 14 working/counter electrode gaps, and solvent was removed in a vacuum chamber to yield a conductive film. This vacuum dropcasting was repeated until each device exhibited a resistance of 1-10 kΩ as measured by a handheld multimeter (in most cases, 1-2 dropcastings achieves this resistance). To apply a selector, 1 µL of a DMF solution of the selector (1 mg/mL) was added to the CNT network and dried under vacuum. For consistency, CNT chemiresistors without added selectors were also treated with 1 µL of pure DMF and dried under vacuum.

Gas Detection Experiments

Analyte gas streams were generated with a KIN-TEK FlexStream gas generator. Unless otherwise noted, liquid analyte was placed in an uncapped (size 15-425) test tube in the analyte oven at 40° C. to generate vapors. The mass loss of the analyte sources over a set period of time was used to calculate emission rates (ng/min), which was then used to convert oven and diluent flow rates into analyte concentrations (ppm). For highly corrosive trifluoroacetic acid and dichloroacetic acid, no attempt to determine an emission rate, to protect against corrosion of the gas generator. Analyte streams were introduced to the sensor in a custom PTFE enclosure. A USB multiplexer (PalmSens) applied a 0.1 V bias across each device and measured the current as a function of time.

Figure 7:
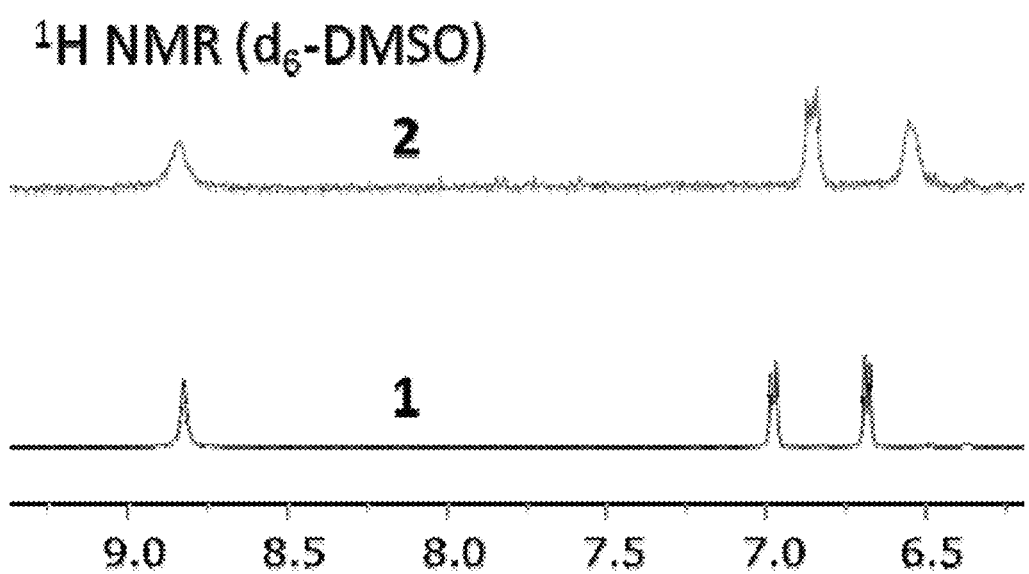
FIG. 7 shows $^1$H NMR spectra of square planar complexes 1 and 2.

Referring to FIG. 7, $^1$H NMR spectra of 1 and 2 are shown.

Figure 8:
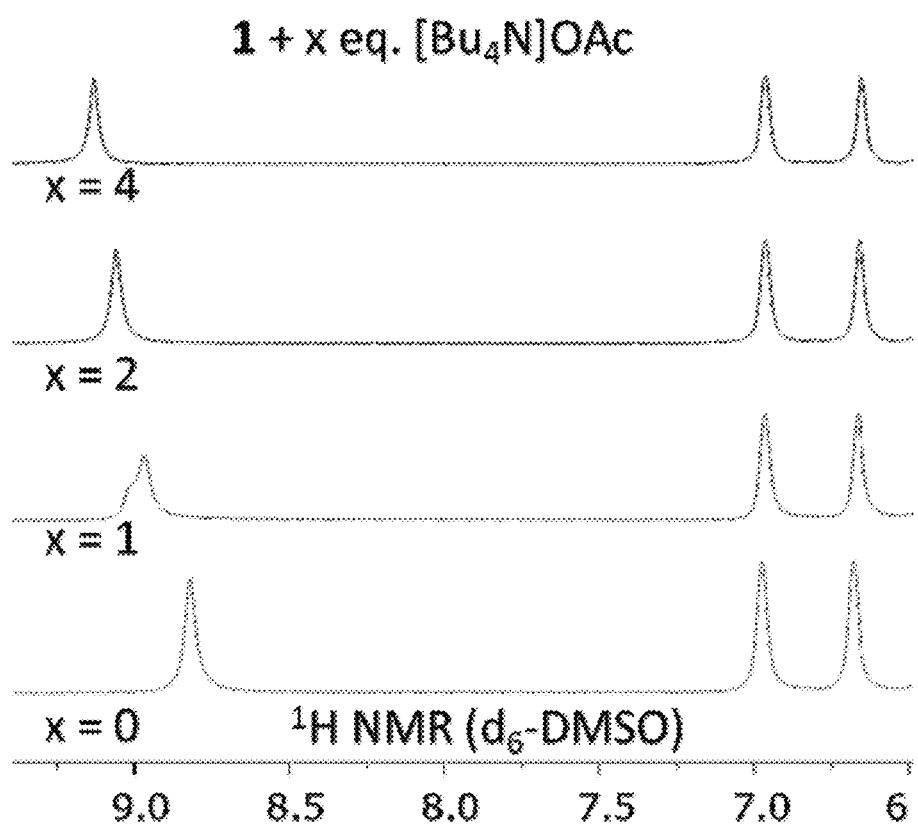
FIG. 8 shows $^1$H NMR spectra (300 MHz) monitoring addition of [Bu4N]OAc to 1.

Referring to FIG. 8, $^1$H NMR spectra (300 MHz) monitoring addition of [Bu4N]OAc to 1 are shown.

Figure 9:
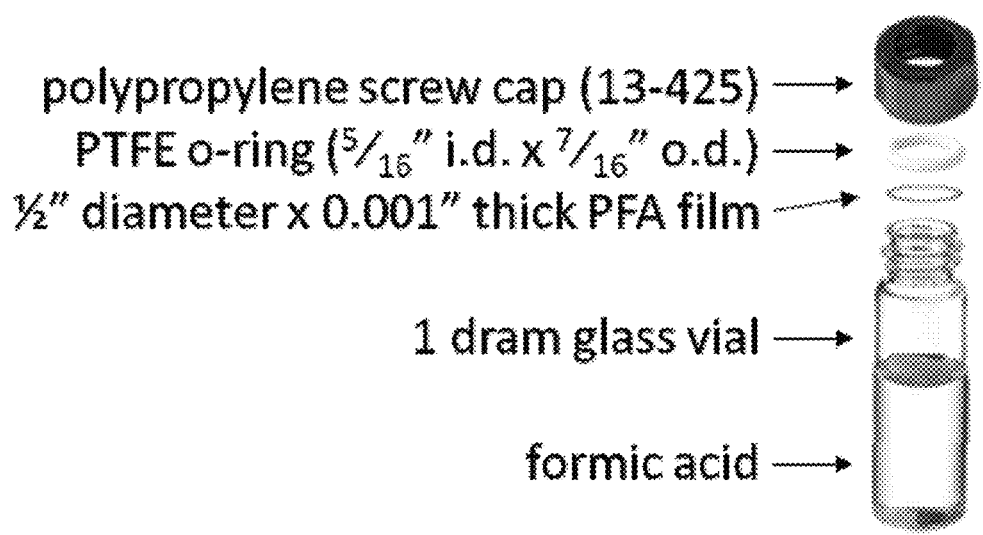
FIG. 9 shows the construction of custom low-emission permeation tube.

Referring to FIG. 9, this shows an exemplary construction of custom low-emission permeation tube. In this embodiment, a polyprolypene screw cap is fitted over the PTFE o-ring, and over the ½ inch diameter×0.001 inch thick PFA film, all over a 1 dram glass vial containing formic acid.

Lower concentrations of formic acid vapor were achieved without excessive diluent flow by construction of a permeation tube, as illustrated in FIG. 9. A 1 dram glass vial with an open-faced screw cap (size 13-425) was filled with formic acid and covered with a 0.5" diameter disc cut from 0.001" thick PFA film (McMaster-Carr) and a PTFE o-ring before being screwed shut. To determine the emission rate of this device, the tube was placed in the analyte oven for 1 h (at 70 sccm oven flow, 40° C. oven temperature) and then an initial mass was recorded. The tube was then kept in the analyte oven for 8.5 days, and an emission rate of 707 ng/min was determined. For comparison, an uncapped (size 15-425) test tube of formic acid under the same oven conditions emits at $2.512 \times 10^5$ ng/min.

Figure 10:
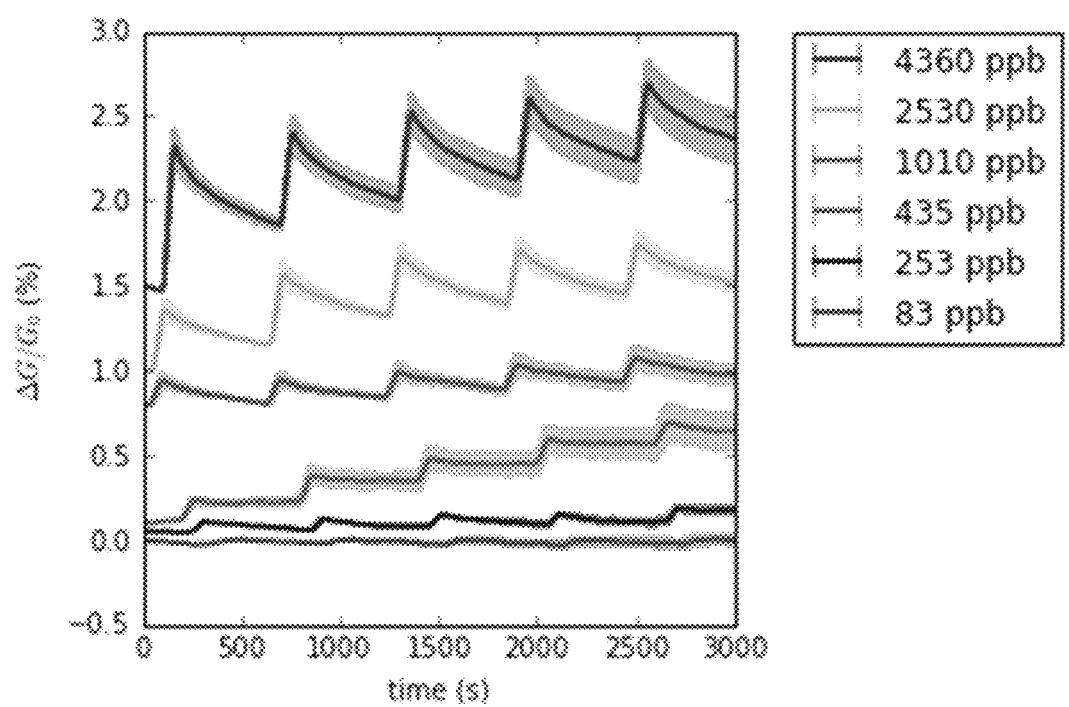
FIG. 10 shows average conductivity traces (N=4) of CNT/1 upon exposure to various concentrations of formic acid vapor.

Referring to FIG. 10, this shows an average conductivity traces (N=4) of CNT/1 upon exposure to various concentrations of formic acid vapor.

The one-minute exposure and nine-minute purge was cycled 5 times. These traces were used to plot the lower six concentration data points on FIG. 3A discussed above.

Figure 11:
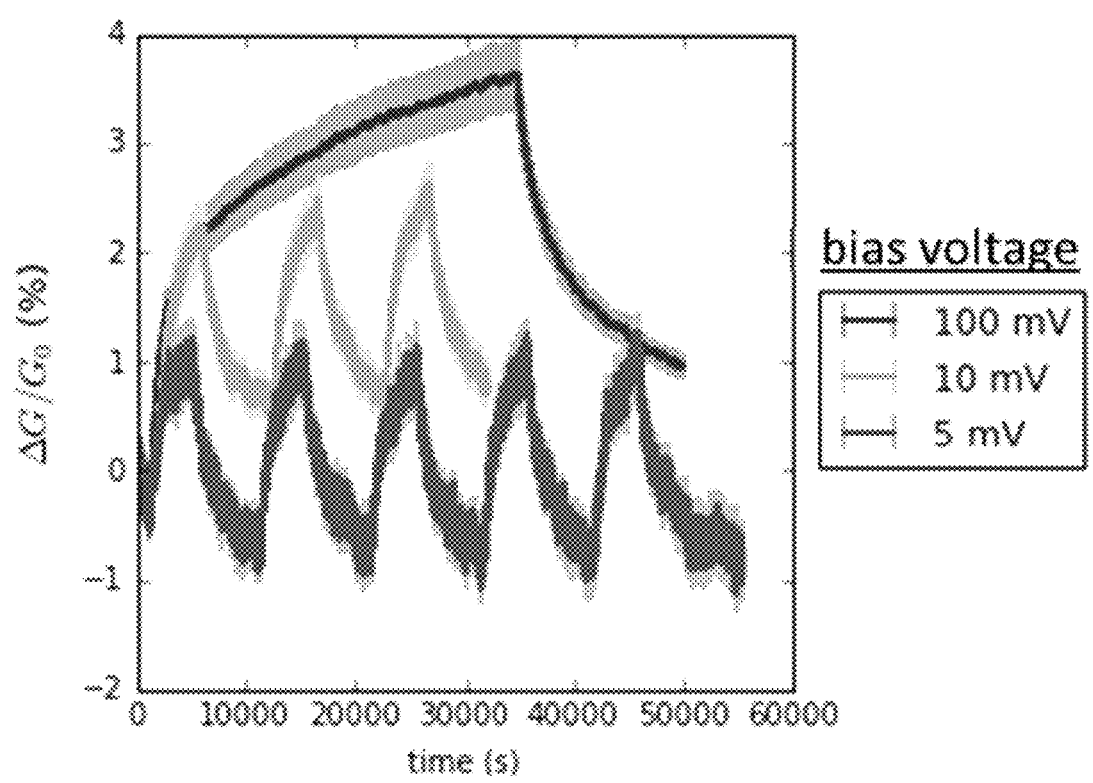
FIG. 11 shows longer formic exposures and effect of varying bias voltage.

Referring to FIG. 11, this shows a longer formic exposures and effect of varying bias voltage.

The chemiresistive response to 3.7 ppm formic acid (0.2% of saturated vapor from 40° C. analyte oven) does not saturate with a 500 min exposure time, but most of the response happens in the beginning (red trace). Lowering the bias voltage yields noisier but similar responses with 50 minute exposures (red, orange, and green traces), supporting that this is a chemiresistive and not a fuel-cell sensor, which would yield lower responses with lower bias voltages.

Figure 12:
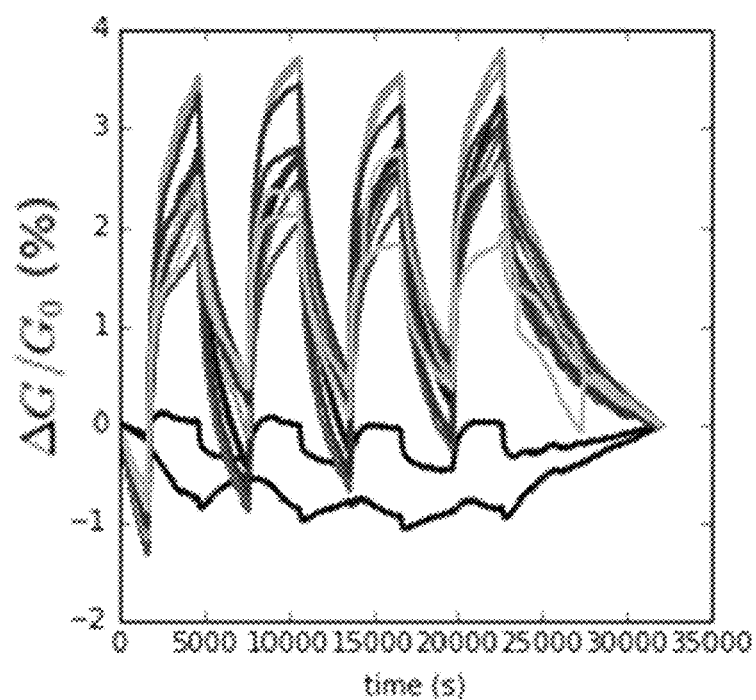
FIG. 12 shows changes in conductivity upon formic acid exposure (37 ppm) as an effect of loading of 1.

Referring to FIG. 12, this shows changes in conductivity upon formic acid exposure (37 ppm) as an effect of loading of 1.

Traces are color-coded by selector loading, with x 1 uL drops of 1 mg/mL 1/DMF applied to the CNT network. The sensing enhancement between x=0 and x=1 was large, with minimal improvements in sensing for x=2-5. Over-loading of the selector (x=6) diminished sensor response.

Referring to FIG. 13, this shows a UV-Vis-NIR absorption spectrum of 1 and 3 in DMF before and after sonication with CNT and filtration.

The CNTs visibly remained mostly aggregated after 1 minute of bath sonication; filtration was performed to eliminate scattering effects.

Referring to FIG. 14, this shows Raman spectra of sensing materials under ambient air or saturated formic acid vapor (FA).

Referring to FIG. 15, this shows 10 cm-1-wide windows of sharp features of Raman spectra of CNT/1.

Figure 16:
FIG. 16 shows a visualization of 640 carbon segments in a (10,10)-CNT.

Referring to FIG. 16, this is an exemplary visualization of 640 carbon segments in a (10,10)-CNT.

Each colored 640 carbon segment corresponds to the region for one protonation of CNT/1 under saturated formic acid vapor, as determined by 0.5 $cm^{-1}$ shift of the Raman spectrum G-band vs. ambient air recording.

Computational Details.

Figure 17:
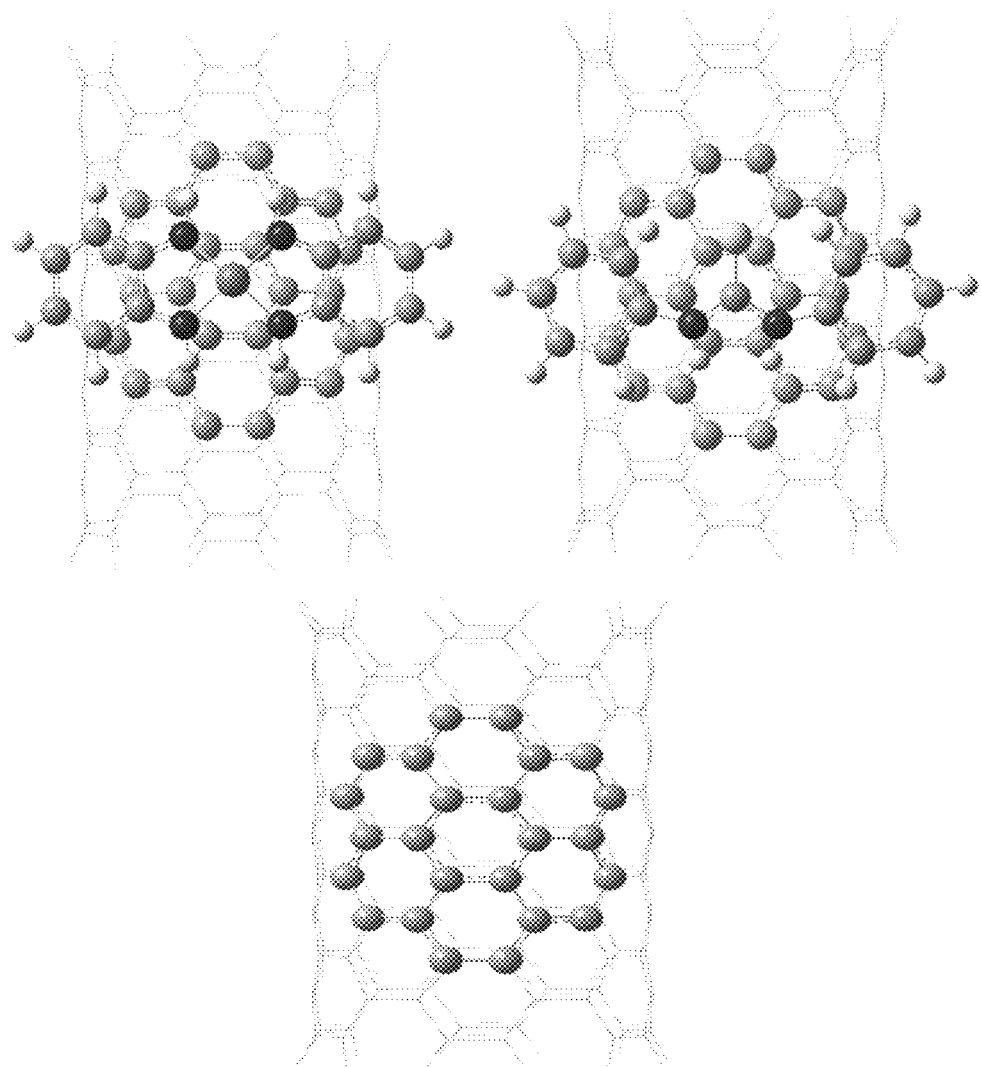
FIG. 17 shows ONIOM-optimized structures.

Initial nanotube coordinates were generated with the Nanotube Builder module of Avogadro. See, e.g., Hanwell, M. D.; Curtis, D. E.; Lonie, D. C.; Vandermeerschd, T.; Zurek, E.; Hutchison, G. R. Avogadro: An Advanced Semantic Chemical Editor, Visualization, and Analysis Platform. *J. Cheminform.* 2012, 4 (8). Geometry optimizations were performed using the Gaussian 09. See, e.g., Ortiz, J. V; Cioslowski, J.; Fox, D. J. Gaussian 09, Revision B. 01. *Wallingford CT* 2009, 1 (2), 3. The ONIOM partitioning schemes are shown in FIG. 17 below. The high-level model was treated with DFT using the ωB97XD functional (see, e.g., Chai, J.-D.; Head-Gordon, M. Long-Range Corrected Hybrid Density Functionals with Damped Atom-atom Dispersion Corrections. *Phys. Chem. Chem. Phys.* 2008, 10 (44), 6615) (with built-in dispersion and long-range corrections) and the 6-31G basis set, (see, e.g., itchfield, R.; Hehre, W. J.; Pople, J. A. Self-Consistent Molecular Orbital Methods. 9. Extended Gaussian-Type Basis for Molecular-Orbital Studies of Organic Molecules. *J. Chem. Phys.* 1971, 54 (2), 724-728) while the low-level model was treated semiempirically with PM6. See, e.g., Stewart, J. J. P. Optimization of Parameters for Semiempirical Methods V: Modification of NDDO Approximations and Application to 70 Elements. *J. Mol. Model.* 2007, 13 (12), 1173-1213. Using the "scf=xqc" keyword assisted the calculations in converging. Optimized structures were then analyzed by a single-point calculation, with all atoms being treated by DFT as implemented in Orca v3.0.3 (see, e.g., Neese, F. The ORCA Program System. *Wiley Interdiscip. Rev. Comput. Mol. Sci.* 2012, 2 (1), 73-78) using the ωB97X-D3 functional, def2-SVP basis set, (see, e.g., Weigend, F.; Ahlrichs, R. Balanced Basis Sets of Split Valence, Triple Zeta Valence and Quadruple Zeta Valence Quality for H to Rn: Design and Assessment of Accuracy. *Phys. Chem. Chem. Phys.* 2005, 7 (18), 3297) and the RIJCOSX Resolution of Identity approximation. While these parameters could find a stable broken-symmetry electronic state for 1 alone (using the Flipspin and FinalMs keywords), (6,6)-CNT/1 converged to a closed-shell solution. Multiwfn was used to translate the Orca calculation output into density-of-states plots and Fermi levels (Gaussian broadening, FWHM=0.300 eV). See, e.g., Lu, T.; Chen, F. Multiwfn: A Multifunctional Wavefunction Analyzer. J. Comput. Chem. 2012, 33 (5), 580-592).

Referring to FIG. 17, this depicts exemplary ONIOM-optimized structures. From left to right, the following is shown: (6,6)-CNT/1, (6,6)-CNT/3, and (6,6)-CNT. Ball-and-stick atoms are assigned to the high-level model (DFT) and the wireframe portion is assigned to the low-level model (PM6).

Figure 18:
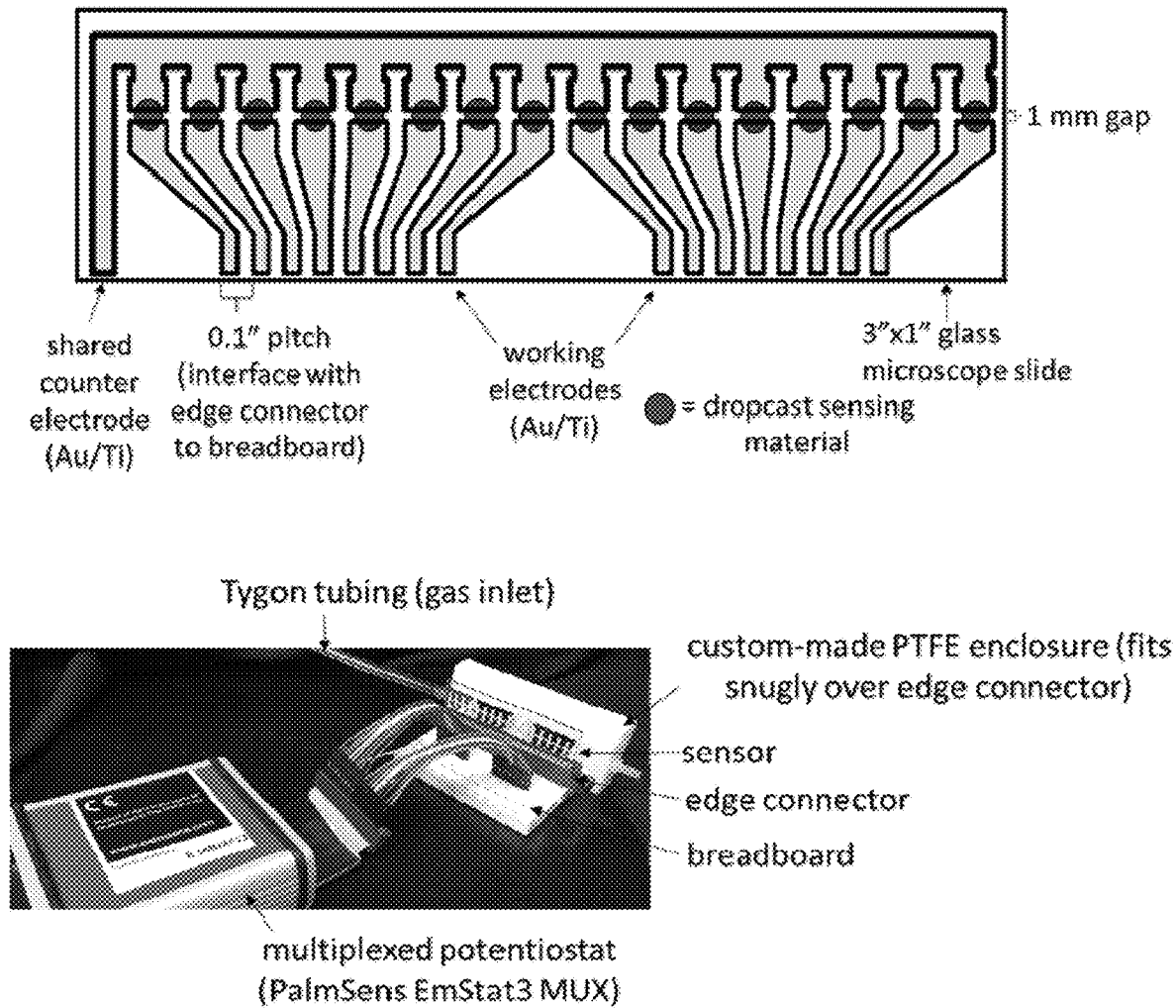
FIG. 18 shows a sensor schematic (top) and a device setup photo (bottom)

Referring to FIG. 18, this shows a sensor schematic (top) and an exemplary device setup depicting a multiplexed potentiostat. A sensor, edge connector and breadboard are shown in this setup. Tygon tubing is used for the gas inlet. Custom-made PTFE enclosures fit snugly over the edge connector.

In the photo, the PTFE enclosure is placed to the side of the sensor for clarity. During operation, the enclosure fits snugly on the edge connector and directs the analyte stream to the sensor chip.

Each of the references cited herein is incorporated by reference in its entirety.

Other embodiments are within the scope of the following claims.

What is claimed is:

1. A method of sensing an analyte comprising:
    exposing a sensor to a sample, the sensor including:
        a conductive region in electrical communication with at least two electrodes, the conductive region including a mixture of a square-planar metal complex and a carbon nanotube;
        measuring an electrical property at the at least two electrodes; and
        detecting formic acid.

2. The method of claim 1, wherein the square-planar metal complex includes a nickel complex.

3. The method of claim 2, wherein the square-planar metal complex includes a palladium complex.

4. The method of claim 2, wherein the square-planar metal complex includes phenylenediamine.

5. The method of claim 1, wherein the carbon nanotube is non-covalently functionalized by the square-planar metal complex.

6. The method of claim 1, wherein the carbon nanotube is a single-walled carbon nanotube.

7. The method of claim 1, wherein the detection is semi-reversible.

8. The method of claim 1, further comprising detecting the analyte below 5 ppm.

9. A method of sensing an analyte comprising:
exposing a sensor to a sample, the sensor including:
a conductive region in electrical communication with at least two electrodes, the conductive region including a mixture of a square-planar metal complex and a carbon nanotube;
measuring an electrical property at the at least two electrodes; and
selectively detecting formic acid.

10. A method of preparing a sensor comprising:
forming a complex including a conductive region in electrical communication with at least two electrodes, the conductive region including a mixture of a square-planar metal complex and a carbon nanotube; and
placing the conductive material in electrical communication with the at least two electrodes
measuring an electrical property at the at least two electrodes; and
selectively detecting formic acid.

11. The method of claim 10, wherein the square-planar metal complex includes two or more selectors.

12. The method of claim 11, wherein the two or more selectors leverage their chelating N—H moieties to facilitate protonation or p-doping of a CNT chemiresistor network by formic acid vapors.

* * * * *